US00PP27927P2

(12) United States Plant Patent
Lane

(10) Patent No.: US PP27,927 P2
(45) Date of Patent: Apr. 25, 2017

(54) SWEET CHERRY TREE NAMED 'SPC243'

(50) Latin Name: *Prunus avium*
Varietal Denomination: SPC243

(71) Applicant: William David Lane, Summerland (CA)

(72) Inventor: William David Lane, Summerland (CA)

(73) Assignee: HER MAJESTY THE QUEEN IN RIGHT OF CANADA AS REPRESENTED BY THE MINISTER AGRICULTURE & AGRI-FOOD, Ontario, Ottawa (CA)

( * ) Notice: Subject to any disclaimer, the term of this patent is extended or adjusted under 35 U.S.C. 154(b) by 120 days.

(21) Appl. No.: 14/545,551

(22) Filed: May 20, 2015

Related U.S. Application Data

(60) Provisional application No. 61/997,081, filed on May 21, 2014.

(51) Int. Cl.
*A01H 5/08* (2006.01)

(52) U.S. Cl.
USPC ..... Plt./181

(58) Field of Classification Search
USPC ..... Plt./156, 180, 181
See application file for complete search history.

(56) References Cited

PUBLICATIONS

PLUTO: Plant Variety Database, Oct. 28, 2016, citation for 'SPC243'. 1 page.*
Integrated Fruit Production Guide : Varieties and Pollination. 2010. www2.gov.bc.ca/assets/gov/farming-natural-resource-and...and.../varieties.pdf. 3 pages.*
Plant Varieties Journal. 2007. Canadian Food Inspection Agency. 65. 5 pages.*

* cited by examiner

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of sweet cherry tree named 'SPC243', that is characterized by its upright growth habit with semi-erect one year-old shoots and sparse crown density, its small fruit that is elongated kidney shaped, its fruit skin that is yellow in color with an orange-red over-color, its fruit flesh that is yellow in color, its moderate to high fruiting precocity, its flowers that are self-fertile, and its late to very late fruit harvest season.

2 Drawing Sheets

Botanical classification: *Prunus avium.*
Variety denomination: 'SPC243'.

BACKGROUND OF THE INVENTION

The present invention relates to a new and distinct cultivar of *Prunus avium* and will be referred to hereafter by its cultivar name, 'SPC243'. 'SPC243' is a new cultivar of sweet cherry tree grown for fruit production.

The new cultivar of *Prunus* arose from a breeding program conducted by the Inventor at a research center in Summerland, BC, Canada with the goal of developing new cultivars of cherry tree that would extend the harvest season with firm, well-sized fruit with good stem pull retention, long storage life, and flowers that are self-fertile.

'SPC243' originated as a seedling that arose from seed planted from open pollination of 'Sumtare' (not patented). 'SPC243' was selected as a single unique tree in 1995 from amongst the resulting seedlings.

Asexual propagation of the new cultivar was first accomplished by chip budding and grafted onto *Prunus avium* rootstock by the Inventor in Summerland, BC, Canada in 1999. Asexual propagation by chip budding and grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SPC243' as a unique cultivar of cherry tree.

1. 'SPC243' exhibits an upright growth habit with semi-erect one year-old shoots and sparse crown density.
2. 'SPC243' exhibits medium fruit that is elongated kidney shaped.
3. 'SPC243' exhibits fruit skin that is yellow in color with an orange-red over color (blush cherry).
4. 'SPC243' exhibits fruit flesh that is yellow in color.
5. 'SPC243' exhibits a moderate to high fruiting precocity.
6. 'SPC243' exhibits flowers that are self-fertile.
7. 'SPC243' exhibits a late to very late fruit harvest season.

'Sumtare', the female parent of 'SPC243', is similar to 'SPC243' in being self-fertile. 'Sumtare' differs from 'SPC243' in having fruit that is round in shape, in having fruit skin that is mahogany in color, in having fruit flesh that is red-purple in color, in having fruit that is larger in size and heavier in weight, and in having fruit that matures earlier. 'SPC243' can be most closely compared to the sweet cherry cultivars '13N0770' (not patented) and 'Rainier' (not patented). '13N0770' is similar to 'SPC243' in being a blush cherry and in being self-fertile. '13N0770' differs from 'SPC243' in having fruit that is flattened cordate in shape, in having fruit flesh that is white in color, in having fruit that is larger in size and heavier in weight, and in having fruit that matures over a week earlier. 'Rainier' is similar to 'SPC243' in being a blush cherry. 'Rainier' differs from 'SPC243' in having fruit that is flat and round in shape, in not being self-fertile, in having fruit that is larger in size and heavier in weight, and in having fruit that matures up to three weeks earlier.

BRIEF DESCRIPTION OF THE DRAWINGS

The accompanying colored photographs illustrate the overall appearance and distinct characteristics of the sweet cherry, 'SPC243'. The photographs were taken of a seven year-old plant of 'SPC243' as grown outdoors in a trial plot in Summerland, BC, Canada.

Figure 1:
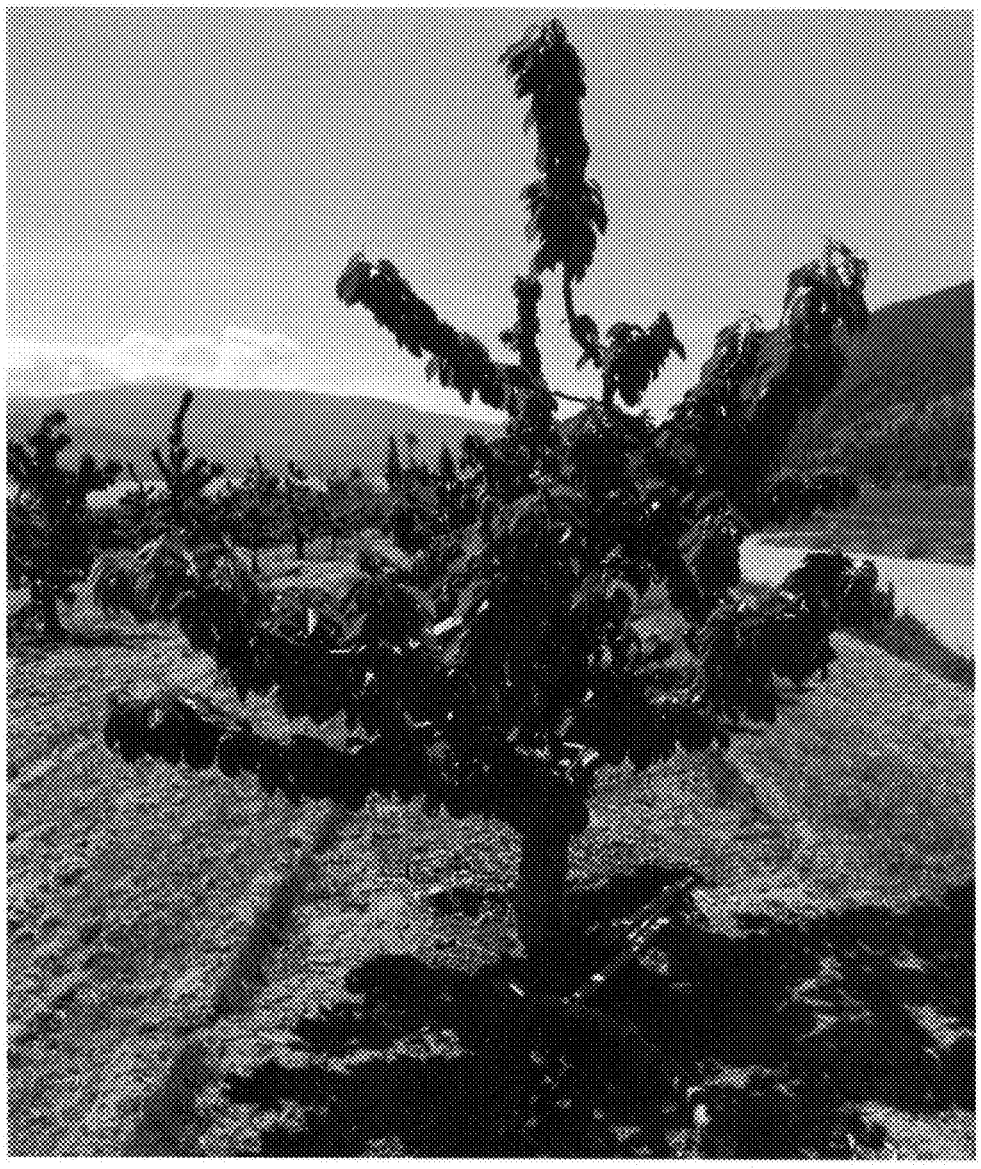
FIG. 1 provides a side view of a plant of 'SPC243'.
Figure 2:
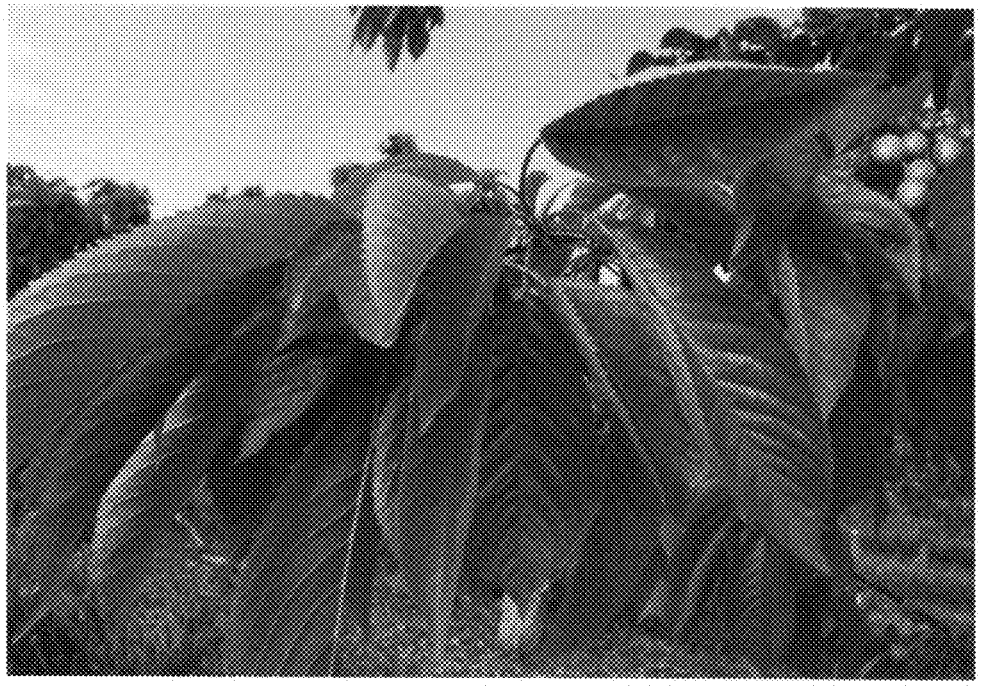
FIG. 2 provides a close-up view of the foliage of 'SPC243'.
Figure 3:
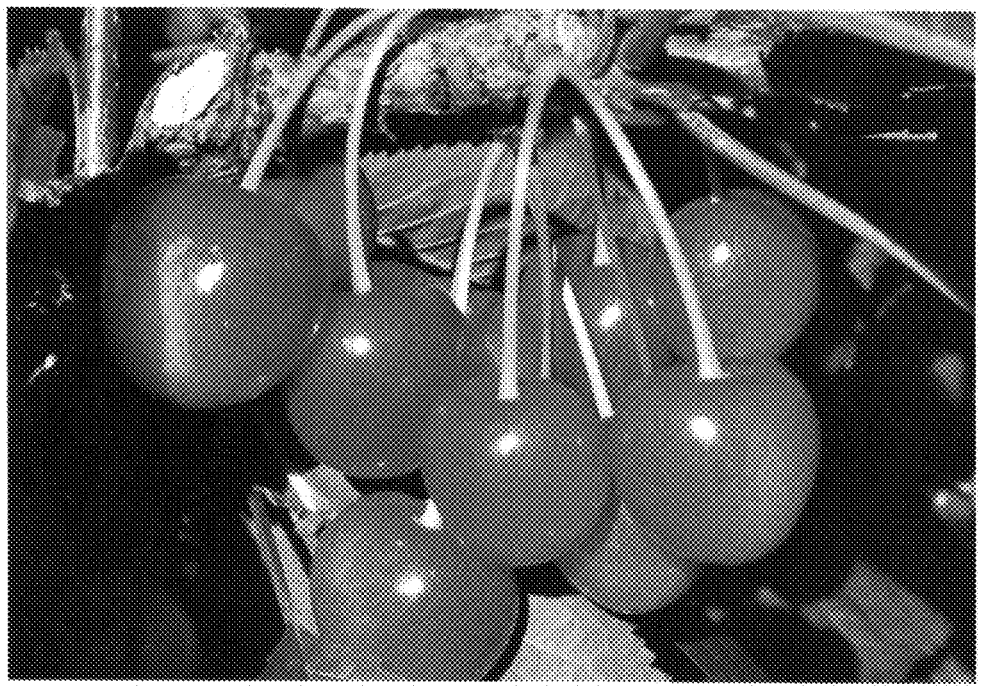
FIG. 3 provides a close-up view of the fruit of 'SPC243'.

The colors in the photographs are as close as possible with the digital photography and printing techniques utilized and the color codes in the detailed botanical description accurately describe the new cherry tree.

DETAILED BOTANICAL DESCRIPTION

The following is a detailed description of seven year-old trees as grown outdoors in a trial plot in Summerland, BC, Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Deciduous fruit bearing tree.

*Plant habit.*—Upright and spreading with semi-erect one year-old shoots and sparse crown density.

*Height and spread.*—Reaches an average of 3.2 m in height and about 3.1 m in width.

*Cold hardiness.*—At least to U.S.D.A. Zone 6A.

*Diseases and pests.*—No susceptibility or resistance to diseases or pests has been observed.

*Root description.*—Fibrous, freely branched.

*Propagation*—Chip budding and grafting.

*Growth rate.*—Vigorous.

Trunk description:

*Size of trunk.*—55.88 cm in diameter measured 40 cm above soil level.

*Bark color.*—155D to 198A with Horizontal stripes of 187A.

*Bark texture.*—Stripes are smooth, grey (198A) portion is rough.

Description of dormant shoots (one year-old):

*Pubescence.*—Absent.

*Shoot size.*—An average of 55 cm in length and 6.3 mm in width.

*Anthocyanin presence.*—Absent.

*Thickness of shoot at center of middle internode.*—Moderate to thick; an average of 6.3 mm.

*Bark color.*—165A.

*Bark surface.*—Smooth with raised lenticels.

*Shoot angle.*—Semi-erect.

*Lenticels.*—Numerous.

*Branch internode length.*—Moderately long; average of 4.4 cm.

*Vegetative buds.*—Moderately large in size; 8 mm in length and 3 mm in width, conical in shape, held slightly out from shoot, moderate to high support.

Description of growing shoots:

*Color of growing tip of shoot.*—145A.

*Pubescence of shoots tip.*—Absent.

*Anthocyanin presence.*—Absent.

*Surface.*—Smooth.

Foliage description:

*Leaf shape.*—Broad ovate to elliptic.

*Leaf division.*—Simple.

*Leaf base.*—Rounded.

*Leaf apex.*—Acute and acuminate to cuspidate at very tip.

*Leaf fragrance.*—None.

*Leaf burst.*—Typically 1$^{st}$ week of May.

*Leaf venation.*—Pinnate, not prominent, same as leaf color with the midrib on upper surface 137A and lower surface 138A.

*Leaf margins.*—Serrate.

*Leaf arrangement.*—Alternate.

*Leaf aspect.*—Concave and held horizontal to slightly downward in relation to shoot.

*Leaf attachment.*—Petiolate.

*Leaf surface.*—Slightly pubescent on lower surface and weak to upper surface moderately glossy on upper surface.

*Leaf size.*—Mature leaves average 16.2 cm in length and 7.0 cm in width.

*Leaf internodes.*—An average of 4.5 cm.

*Leaf color.*—Newly expanded leaves upper surface; 152B, newly expanded leaves lower surface; 146B, leaves are fringed with 187A, mature leaves upper surface; 137A, mature leaves lower surface; 138A.

*Petioles.*—Average of 3.81 cm in length and 2.44 mm in width, 182B to 145A in color with anthocyanin 187A, typically 3 nectarines that are kidney-shaped and 168C to 184C in color, glabrous surface.

Inflorescence description:

*Blooming period.*—Blooms on average in the middle of the cherry bloom period in B.C., Canada.

*Inflorescence type.*—Clusters of single flowers.

*Lastingness of inflorescence.*—14 days.

*Flower fragrance.*—Minimal.

*Flower quantity.*—2 to 3 per cluster.

*Flower type.*—Rotate corolla above an elongated calyx with stamens and pistil extended.

*Flower size.*—Large; an average of 3.9 cm in diameter.

*Calyx.*—Comprised of sepals fused into an ovoid base with un-fused portions spreading at apex.

*Sepals.*—5, yellow-green 144B in color, glabrous on both surfaces, about 6.7 mm in length with un-fused portions about 41 mm in width and length, entire glandular margin, attenuate apex, fused base.

*Petals.*—5, obovate in shape, un-fused, overlapping, entire margin, oblique base, retuse apex, about 1.7 cm in length and 1.3 cm in width, 155D in color (upper and lower surface), smooth on upper and lower surface.

*Pedicels.*—Average of 26.8 mm in length, 1.1 mm in width, 144B in color, glabrous surface.

*Flowers lightly compacted with whorled arrangement.*

Reproductive organs:

*Gynoecium.*—1 pistil about 1.4 cm in length and <1 mm in width extending beyond perianth, style is 144D in color and about 1 mm in length, stigma is about <1 mm in diameter and 164C in color, ovary is superior, glabrous and 144C in color.

*Androcoecium.*—Average of 30 stamens, base adnate to calyx, filaments are white group 155D in color, about 12 mm in length and <1 mm in width, anthers are 22C in color, dorsifixed, about <1 mm in length and in width, pollen is abundant in quantity and about 22C in color.

*Fertility.*—Self-fertile.

Fruit description:

*Fruit type.*—Drupe.

*Fruit shape.*—Kidney-shaped (lateral view is flattened), flat apex.

*Fruit apex.*—Flat with low susceptibility to rain induced cracking.

*Fruit size.*—Very large; 2.42 cm in length and 2.46 cm in width.

*Fruit firmness.*—Firm.

*Fruit set.*—High.

*Fruit stalk.*—Long; average of 4.68 cm in length and 1.38 cm in wide, surface color 144B.

*Fruit bearing.*—Medium to high.

*No of fruit per cluster.*—Ten.

*Skin color.*—A blend of 46B and 16D when ripe with light colored dots.

*Skin suture.*—Moderate prominence.

*Harvest date.*—Very late harvest season; last week in August in Summerland, BC, Canada.

*Skin surface.*—Glossy.

*Flesh color.*—163D.

*Flesh texture.*—Fleshy, moderately juicy.

*Flavor.*—Medium degree of sweetness.

*Weight.*—An average of 8.97 g/berry.

*Brix.*—18.5%.

*Acidity.*—Low to medium.

*Fruit productivity.*—An average of 10 tons per acre on a mature tree.

*Fruit storage.*—Stores in Modified Atmospheric Packaging for at least 5 weeks at 1° C.

*Seeds.*—1 stone per berry, 165C in color, large in size; average of 8.61 mm in length and 10.60 mm in width, 1.19 cm in length semi adherent to flesh, shape; lateral view is symmetrical and spherical to elongate, front view is elliptic, basal view is round, keel is very strongly developed.

It is claimed:

1. A new and distinct cultivar of Sweet cherry tree named 'SPC243' as herein illustrated and described.

* * * * *